(12) United States Patent
Josephson et al.

(10) Patent No.: US 8,096,940 B2
(45) Date of Patent: *Jan. 17, 2012

(54) REPRODUCTIVE MANAGEMENT

(75) Inventors: Scott D. Josephson, Taunton, MN (US);
Bruce James Iverson, Garvin, MN (US); Rodney A. Schulze, Holland, MN (US)

(73) Assignee: Iversync II LLC, Holland, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/767,244

(22) Filed: Apr. 26, 2010

(65) Prior Publication Data

US 2010/0234677 A1 Sep. 16, 2010

Related U.S. Application Data

(63) Continuation-in-part of application No. 11/584,010, filed on Oct. 19, 2006, now Pat. No. 7,732,408.

(60) Provisional application No. 60/728,076, filed on Oct. 19, 2005.

(51) Int. Cl.
*A61D 19/02* (2006.01)
*A61D 19/00* (2006.01)
*A61K 31/56* (2006.01)

(52) U.S. Cl. .............................. 600/35; 600/33; 514/177
(58) Field of Classification Search .................... 600/33, 600/35; 514/177
See application file for complete search history.

(56) References Cited

U.S. PATENT DOCUMENTS

| | | | |
|---|---|---|---|
| 4,089,951 A | 5/1978 | Furr | |
| 5,589,457 A | 12/1996 | Wilbank et al. | |
| 6,423,039 B1 | 7/2002 | Rathbone et al. | |
| 7,208,265 B1 * | 4/2007 | Schenk | 435/1.1 |
| 2003/0059951 A1 | 3/2003 | Frushour et al. | |

OTHER PUBLICATIONS

Rensis et al. (Theriogenography. 2002; 58: 1675-1687).*
Pfizer Animal Health, Dairy Overview for CIDR, Internet Page, printed on Jul. 25, 2007, http://www.cidr.com/product_overview.asp?country=US&lang=EN&species=DA&drug=CI.
Pfizer Animal Health, Dairy Detail for CIDR, Internet Page, printed on Jul. 26, 2007, http://www.cidr.com/product_detail.asp?country=US&lang=EN&species=DA&drug=CI.
Dec International, Product Information for CIDR, Drug Information Sheet, available at http://www.cidr.com/PAHimages/compliance_pdfs/US_EN_CI_compliance.pdf, (Aug. 2003).
Pharmacia & Upjohn, Material Safety Data Sheet for CIDR, Apr. 4, 2002, available at http://www.cidr.com/PAHimages/msds_us/CI.pdf.
Pfizer Animal Health, Answers to Frequently Asked Questions about CIDR, Internet Page, printed on Jul. 25, 2007, http://www.cidr.com/QandA.asp?country=US&lang=EN&species=DA&drug=CI.
Pfizer Animal Health, Dairy Overview for LUTALYSE, Internet Page, printed on Jul. 25, 2007, http://www.lutalyse.com/product_detail.asp?country=US&lang=EN&species=DA&drug=LT.
Pfizer Animal Health, Dairy Detail for LUTALYSE, Internet Page, printed on Jul. 25, 2007, http://www.lutalyse.com/product_detail.asp?country=US&lang=EN&species=DA&drug=LT.
Pharmacia & Upjohn, Product Information for LUTALYSE, Drug Information Sheet, Jun. 2004, available at http://www.lutalyse.com/PAHimages/compliance_pdfs/US_EN_LT_compliance.pdf.
Pharmacia & Upjohn, Material Safety Data Sheet for LUTALYSE, Jun. 23, 1997, available at http://www.lutalyse.com/pahimages/msds_us/Lutalyse.pdf.
Pfizer Animal Health, Answers to Frequently Asked Questions about LUTALYSE, Internet Page, printed on Jul. 25, 2007 http://www.lutalyse.com/QandA.asp?country=US&lang=EN&species=DA&drug=LT.
Fricke, Paul M., Reproductive Management of Dairy Heifers, available at http://www.wisc.edu/dysci/uwex/rep_phys/pubs/heifers502.pdf, (prior to Apr. 2, 2005).
Cordoba, M. C., Sartori, R., & Fricke, P. M., Assessment of a Commercially Available Early Conception Factor (ECF) Test for Determining Pregnancy Status of Dairy Cattle, J. Dairy Sci., Aug. 2001 84(8):1884-9.
Merial, Product Information for CYSTORELIN, Drug Information Sheet, available at http://merialusa.naccvp.com/view.php-?prodnum=1111008, (Mar. 2005).
Merial, General Information for CYSTORELIN, Internet page, printed on Jul. 26, 2007, http://us.merial.com/producers/dairy/products_cystorelin.asp#.
Schering-Plough Animal Health, Drug Information Sheet for Estrumate, available at http://www.mycattle.com/estrumate/S517-005310_EST_50dose_SS_04.pdf, (1999).
EDP Biotech Corp., General Information for EDP/ECF, Internet page, printed on Jul. 26, 2007, http://edpbiotech.com/our_products/veterinarian_diagnostics/cow_testing/cow_testing.html.
EDP Biotech Corp., EDP/ECF Frequently Asked Questions, Internet page, printed on Jul. 26, 2007, http://edpbiotech.com/our_products/veterinarian_diagnostics/cow_testing/faqs/faqs.html.
International Search Report for PCT/US06/40832, dated Mar. 28, 2008.
Written Opinion of the International Searching Authority; PCT Application No. PCT/US06/40832, dated Mar. 25, 2009.
Application and File history for U.S. Appl. No. 11/584,010, filed Oct. 19, 2006. Inventors: Josephson et al. at www.uspto.gov.

* cited by examiner

*Primary Examiner* — Shanon A Foley
(74) *Attorney, Agent, or Firm* — Patterson Thuente Christensen Pedersen P.A.

(57) ABSTRACT

A method for breeding bovines, especially a method for breeding dairy and beef cattle without use of heat detection prior to insemination or embryo implantation.

20 Claims, No Drawings

REPRODUCTIVE MANAGEMENT

The present application is a continuation-in-part of U.S. patent application Ser. No. 11/584,010 filed Oct. 19, 2006, now U.S. Pat. No. 7,732,408, which claims the benefit of Provisional Application No. 60/728,076 filed Oct. 19, 2005, both of which are incorporated herein in their entirety by reference.

FIELD OF THE INVENTION

The invention is directed toward breeding methods for bovines, particularly dairy and/or beef cattle, including lactating dairy and/or beef cattle.

BACKGROUND OF THE INVENTION

Dairy cattle operations require efficient breeding regimens for optimal performance and economic yield. Milk production is dependent on cows in the operation becoming pregnant, giving birth and lactating. After birth a cow can be milked for over two hundred days. However, after about 150 days post parturition, the amount of milk produced begins to fall off rapidly. Thus, minimizing the period of time between calving and the beginning of the next pregnancy increases the value of the cow to the dairy operation.

Moreover, the economic value to a dairy operation of a typical cow decreases rapidly thirty six months after first calving. Increasing the number of pregnancies that a cow has during this time maximizes the return on investment in the animal in terms of feed, overhead and other costs.

In recent years, several hormone products have come on the market for manipulation of the estrus cycle in cows. These products include gonadotropin releasing hormone (GnRH), lutenizing hormone LH, prostaglandin F2α, estrogen, progesterone and synthetic analogs of certain of these hormone. Each of these products are used at various times in the estrus cycle to encourage ovulation or otherwise aid in conception and maintenance of pregnancy.

Progesterone levels may elevated in cows by use of exogenously applied progesterone and used, for example, to synchronize estrus in a herd. Application or treatment is conveniently done using a vaginal insert that is constructed to release progesterone at a steady rate. The EAZI-BREED™ CIDR® is produced by DEC International, NZ Ltd. and available in the U.S. from Pfizer Animal Health Products (New York, N.Y.). The CIDR insert is indicated for protocols that allow for synchronization of the a cow's estrus cycle thereby giving the dairy cattle operation a better chance of detecting heat in the cows by narrowing the window in which to place the cow under increased scrutiny. Indeed, the protocols for which the CIDR insert are approved require heat detection to determine optimal time for artificial insemination. For example, in the FAST BACK[SM] method for lactating dairy cows, a cow undergoes artificial insemination and a CIDR insert is administered fourteen days later. At Day 21, the CIDR is removed and the animal is observed over Days 22-25 for heat detection and inseminated on observation of heat. However, use of prostaglandins (such a LUTALYSE®) are contraindicated in this protocol.

Unfortunately, heat detection is difficult, requires proper training and experience to do correctly and is time consuming for the operator and employees in a dairy operation. Some authorities recommend observation of the animals at least three times daily. Certain signs of heat, such as standing heat, may only be present for ten hours within a single estrus cycle. Many signs of heat are also subtle and easy to miss. Large dairy operations often employ many unskilled workers who do not have the necessary training to carry out heat detection. Some estimates place failure of heat detection at or higher than 50%. Missing an observed heat means another estrus cycle must occur before breeding can be attempted again.

Some methods, such as the Ovsynch method have proposed estrus cycle modification using certain hormone injection regimens and the elimination of heat detection. However, at least one evaluation of the Ovsynch method has shown that the method does not give acceptable rates of conception using a fixed-time artificial insemination without heat detection. See, e.g., "Reproductive Management of Dairy Heifers" by Paul M. Fricke, Ph.D. of the Department of Dairy Science, University of Wisconsin-Madison.

Thus, a method is needed to ensure increased breeding efficiency with reduction in the number of months in the breeding cycle without the need for heat detection prior to breeding.

SUMMARY OF THE INVENTION

According to one aspect of the invention, dairy cows are inseminated at a suitable time after maturation or parturition, progesterone is administered nineteen days after insemination, ultrasound is performed on the cow twenty six days after insemination a determination is made whether the cow is open. Ultrasound may be performed no earlier than twenty seven or twenty six days after insemination. Progesterone may administered to the cow nine days before insemination by application of a vaginal insert or other route. Where a vaginal insert is used for administration, the insert is removed two days before insemination. Gonadotropin releasing hormone may also be administered to the cow nine days before insemination. Prostaglandin F2α or cloprostentol may also be administered to the cow two days before insemination. If the cow is open after insemination, the step of the method may be repeated.

In another aspect of the invention, dairy cows that are of suitable maturity and have been open a suitable period may be bred by a method wherein a first progesterone dose is administered to the cow. The cow is then inseminated nine days after administration of the first progesterone dose. A biological specimen is obtained from the cow at least seven and up to thirty days after insemination. At least one assay is performed on the biological sample and a determination is made whether the cow is open based on the result from the assay. A second progesterone dose may be administered twelve days after insemination to a cow that is determined to be open and the cow may be inseminated nine days after the second progesterone dose. The progesterone doses may be administered by application of a vaginal insert and the vaginal inserts may be left in for seven days. Gonadotropin releasing hormone may be administered to the cow nine days before insemination. Prostaglandin F2α or cloprostentol may be administered to the cow two days before insemination.

In yet another aspect of the invention, dairy cattle may be bred by administering a first progesterone device to a cow, administering a first gonadotropin releasing hormone dose to the cow on the same day, then removing the progesterone device and injecting prostaglandin 6 to 8 days later, administering a second gonadotropin releasing hormone dose to the cow nine days after administration of the first gonadotropin releasing hormone dose, implanting an embryo into the cow seven days after the second gonadotropin releasing hormone dose, and administering a second progesterone dose to the cow on the same day as the embryo is placed. This progesterone device remains for fourteen to eighteen days and then is removed nine days prior to the scheduled ultrasound/transfer date. Ultrasound may be performed on the cow thirty nine to forty three days after the first progesterone dose and if the cow is determined to not be pregnant, an embryo may be transferred on the same day s the ultrasound is performed. Where the cow is determined to be open (not pregnant), an embryo may be implanted into the open cow forty two days after the first progesterone dose. The first and second progesterone doses may be administered using a vaginal insert over a period of seven days. Prostaglandin F2α or cloprostentol may be administered to the cow seven days after the first progesterone dose.

DETAILED DESCRIPTION OF THE INVENTION

It has been shown by the inventor that the use of a progesterone insert nineteen days after artificial insemination service in female bovines, for example dairy cattle, along with early pregnancy detection (e.g. six to eight days after insertion or 25 to 27 days after AI service) can reduce the number of AI services required per conception, can decrease the number of days open and can allow the operator of a dairy operation to reduce the number of average days in milk in a herd. The early pregnancy detection may be performed using ultrasound imaging.

In another aspect of the invention, detection of pregnancy may be performed even sooner after AI service. Such detection may utilize methods for detection of biological markers of pregnancy, such as Early Conception Factor. Reagents for performing such detection methods are becoming increasingly available, allowing for detection in multiple animals on an economically acceptable basis. Of course, external factors such as weather, quantity and quality of feed rations, animal handling practices (including penning), facility and equipment management will also have a direct impact on the success of a breeding program using the method of the invention. Heat stress is widely known to decrease conception and full term pregnancy in dairy cattle.

Animal handling practice can have a substantial impact as well on breeding efforts. Cows need sure footing underneath. Penning practices are also important. To the extent possible, cows should be kept in the same groups to maintain stability of favorable social interactions unless other factors such as health concerns interfere. Efforts should also be made to keep cows in facilities where they are not in crowded conditions.

The invention can be more fully understood by reference to the following examples.

EXAMPLE 1

Cows are selected for breeding, typically at a point 50 days from birth (parturition). However, this voluntary waiting period may be 60, 70 or even 100 days after giving birth depending on management practices of a particular dairy operation. At Day 0 of the procedure, a progesterone insert is placed vaginally into the cow to be bred. The cow is also given 2 cc (~100 mcg) of gonadotropin releasing hormone (GnRH) as indicated by the manufacturer, typically by intramuscular (IM) injection. The progesterone insert may be an EAZI-BREED™ CIDR® cattle insert. The GnRH may be CYSTORELIN® GnRH available from Merial Limited, Duluth, Ga. On Day 7, the progesterone insert is removed and 25 mg of dinoprost (prostaglandin F2α) is administered as indicated by the manufacturer, typically by IM injection. The dinoprost may be obtained under the LUTALYZE® brand name from Pfizer Animal Health Products as a dinoprost tromethamine sterile solution.

At Day 9, the cow undergoes artificial insemination (AI) service using standard methods and 50 to 100 mcg GnRH is administered. On Day 28 (19 days post breeding), a progesterone insert is again administered vaginally and 100 mcg of GnRH is administered to the cow by IM injection. At Day 35 (26 days post breeding) the progesterone insert is removed and the cow is checked by ultrasound to determine whether or not the cow is open. Open cows are returned to the treatment cycle described at Day 7. Cows identified as pregnant may then be re-evaluated by ultrasound at Day 42 (33 days post breeding) to confirm pregnancy status. Cows identified as not-pregnant may be treated with a progesterone insert again administered vaginally. In addition, 100 mcg of GnRH may be administered to the cow by IM injection. Alternatively, if personnel and equipment are available at Day 42, cows identified as pregnant may be treated at Day 42 (33 days post-breeding) with a progesterone device administered vaginally. In addition, 100 mcg GnRH may be administered by IM injection. At Day 49 (40 days post-breeding), the progesterone insert is removed and the cow is checked by ultrasound to verify pregnancy. Open cows are returned to Day 7 of the protocol. Finally, pregnancy is again confirmed by ultrasound at Day 70 (61 days post breeding.)

Variations of this method will be obvious to those skilled in the art. However, the most important step in this method is the introduction of exogenous progesterone into the cow at Day 19. This step, combined with the early pregnancy check at Day 26, allows for rapid reentry into an AI servicing schedule thereby reducing days open for all cows being treated with this method. Without being limited by any particular theory, it is believed that the reintroduction of progesterone during the early stages of pregnancy may increase survival rates for these pregnancies.

EXAMPLE 2

Cows are selected for breeding, typically at a point 50 days from birth (parturition). However, this voluntary waiting period may be 60, 70 or even 100 days after giving birth depending on management practices of a particular dairy operation. At Day 0 of the procedure, a progesterone insert is placed vaginally into the cow to be bred. The cow is also given 2 cc (~100 mcg) of gonadotropin releasing hormone (GnRH) as indicated by the manufacturer, typically by intramuscular (IM) injection. The progesterone insert may be an EAZI-BREED™ CIDR® cattle insert. On Day 7, the progesterone insert is removed and 2 cc (25 μg) of cloprostentol (structurally related prostaglandin F2α) is administered as indicated by the manufacturer, typically by IM injection or subcutaneous injection in the anterior half of the neck. The cloprostentol may be obtained under the ESTRUMATE® brand name from Schering-Plough Animal Health Ltd. Wellington, New Zealand. At Day 9, the cow receives artificial insemination (AI) service using standard methods and 100 μg GnRH (e.g. CYSTORELIN) is administered. On Day 16 biological samples (e.g. blood or first strip milk samples) are taken for each cow impregnated at Day 9 and the samples are then evaluated using one or more assays to determine whether the cow is open. Other bioassay tests to determine pregnancy status include those using interferon-stimulated genes (ISG) and pregnancy associated glycoproteins (PAG) and progesterone. The assay may be performed using an EDP/ECF™ early conception factor test. This test is available from EDP Biotech Corporation, Knoxville, Tenn. Alternatively, the EDP/ECF™ early conception factor test could be administered anytime between Day 16 and Day 21. On Day 21, all cows identified as open receive a progesterone insert, 100 μg GnRH and are returned to Day 0 of the protocol.

On Day 28 (19 days post AI), a progesterone insert is again administered vaginally and 100 mcg of GnRH is administered to the cow. At Day 35 (26 days post AI) and the cow is checked by ultrasound to determine whether or not the cow is open. Open cows have the progesterone insert removed are returned to the treatment cycle described at Day 7. The progesterone insert is left in the cows that are pregnant. Again at Day 42 (33 days post AI) a pregnancy test is again performed on the cows that were pregnant on Day 26. The progesterone insert is removed from all cows. If a cow is open, 2 cc of ESTRU-MATE prostaglandin is administered and the cow is returned to Day 7 of the protocol. At Day 63 (54 days post AI), another pregnancy check is administered. Open cows are returned to Day 0 of the protocol. By use of the EDP/ECF™ test at Day 16 to identify open cows and the return of those open cows to Day 0 of the protocol, the cows are bred more efficiently and the number of days open should be fewer. Again, the AI service on Day 9 is done in the absence of heat detection, behavioral or otherwise.

EXAMPLE 3

Another aspect of the invention is the facilitation the transfer of large groups of timed embryo transfers to recipient cows on dairy farms without relying on the expression of heats or heat detection.

The transfer of viable embryos (such as 7-day embryos) into recipient females allows for the recipient cow the opportunity to become pregnant regardless of the quality of her own oocytes. For example, cows under metabolic stress due to overcrowding, comfort issues, weather stress, nutritional stress and post-partum difficulties tend to produce lower quality oocytes which as a result have a lower viability both as fertilizable oocytes and as developing embryos. By placing a higher quality embryo in these cows, the chances for a successful pregnancy are believed to be improved and as a result, overall herd reproductive parameters would likewise also be improved. Furthermore, this system allows for the large scale introduction of new genetics into a herd and can be used with programs that produce large numbers of same or similar genetics sex-selected (e.g. female) embryos to increase the number and quality of replacements in a herd.

At Day 0 of the procedure, a progesterone insert is placed vaginally into the cow to be bred. The cow is also given gonadotropin releasing hormone (GnRH) (e.g. 2 cc (~100 mcg)) as indicated by the manufacturer, typically by intramuscular (IM) injection. The progesterone insert may be an EAZI-BREED™ CIDR® cattle insert. The GnRH may be CYSTORELIN® GnRH available from Merial Limited, Duluth, Ga. On Day 7, the progesterone insert is removed and 25 mg of dinoprost (prostaglandin F2α) or cloprostenol (structurally related prostaglandin F2α) is administered as indicated by the manufacturer, typically by IM injection. The dinoprost may be obtained under the LUTALYZE® brand name from Pfizer Animal Health Products as a dinoprost tromethamine sterile solution. On Day 9, GnRH (e.g. 75 mcg) is administered to the cow. On Day 16, embryo transfer is performed. The transfer may be accomplished using standard procedures for such transfers.

On Day 28, a progesterone insert is administered to the cow. The cow is also given gonadotropin releasing hormone (e.g. 2 cc (~100 mcg)) as described above. On Day 35, the progesterone insert is removed and a pregnancy check is performed using ultrasound. Cows that are determined to be open are returned to Day 7 of the protocol. Cows that are determined to be pregnant are rechecked for pregnancy seven days later (i.e. Day 42). Cows that are determined to be open at Day 42 are returned to Day 0 of the protocol. Cows that are determined to be pregnant are rechecked for pregnancy twenty days later (i.e. Day 63). Cows that are determined to be open at Day 63 are returned to Day 0 of the protocol. While certain numbers of days for accomplishing certain steps are specified herein, one skilled in the art will recognize that deviation slightly from the exact numbers will be possible. Many of the numbers, however, are specified to allow for regular weekly treatment of herds. This regular treatment may allow for convenient scheduling of professional services, especially veterinary service. Therefore, it will be appreciated that various changes can be made therein without departing from the spirit and scope of the invention.

EXAMPLE 4

Another aspect of the invention is the facilitation to provide for the early identification of open ("non-pregnant") recipient cows and subsequent transfer of another embryo on the same day that these cows are identified as non-pregnant. This requires that the non-pregnant cows be 7 to 8 days post-estrus on the day that pregnancy status is determined.

At Day 0 of the procedure, a progesterone insert is placed vaginally into the cow to be bred. The cow is also given gonadotropin releasing hormone (GnRH) (e.g. 2 cc (~100 mcg)) as indicated by the manufacturer, typically by intramuscular (IM) injection. The progesterone insert may be an EAZI-BREED™ CIDR® cattle insert. The GnRH may be CYSTORELIN® GnRH available from Merial Limited, Duluth, Ga. On Day 7, the progesterone insert is removed and dinoprost (prostaglandin F2α) or cloprostenol (structurally related prostaglandin F2α) is administered (e.g. 5 cc (~25 mg)) as indicated by the manufacturer, typically by IM injection. The dinoprost may be obtained under the LUTALYSE® brand name from Pfizer Animal Health Products as a dinoprost tromethamine sterile solution. On Day 9, GnRH (e.g. 1 cc (~75 mcg)) is administered to the cow. On Day 16, embryo transfer is performed. The transfer may be accomplished using standard procedures for such transfers. On Day 16, a progesterone insert is administered to the cow. The progesterone insert is allowed to remain in place for 14 to 18 days, depending on the specific resynchronization schedule, such that it is removed between Day 30 and Day 34, which is about 9 to 10 days prior to pregnancy check, and subsequent embryo implantation if needed. Thus, between Day 39 and Day 44, pregnancy check is performed on the cow using ultrasound. A cow that is determined not to be pregnant is then evaluated for the presence of a functional corpus luteum. If the cow has a suitable corpus luteum, indicating synchrony for embryo transfer, the cow is returned to Day 16 and an embryo is non-surgically implanted using standard transfer techniques. The cow can also be prepared for resynchronization by administering another progesterone insert upon embryo implantation. Cows that are determined to be pregnant are rechecked for pregnancy seven days later (i.e. Day 47). Cows that are determined to be open at Day 47 are returned to Day 0 of the protocol.

Variations of this method will be obvious to those skilled in the art. For example, it is noted that in some embodiments, no dinoprost or cloprostenol injections are administered to the cow upon Day 16 when the embryo implantation is performed and the progesterone insert is administered, and Day 30 when the progesterone insert is removed. The goal of this intense schedule is to narrow the calving season for a group of recipient cows, thus resulting in more embryo transfer calves being born in a shorter time frame for a given group of recipient cows. This results in a more uniform calf crop and more efficient use of cows determined to be used only as recipients.

Another benefit of this protocol is a savings in injectable hormone products typically used in synchronization protocols. This schedule uses only the progesterone insert being administered to resynchronize the recipients without the need of injecting hormone products, such as GnRH or prostaglandin F2α. As such, recipient cows are only handled once rather than three times between embryo transfers.

Comparing this protocol to conventional pregnancy evaluation and resynchronization schedules shows a reduction of about 16 days between embryo transfer dates on non-pregnant recipients. Since conception rates are as high, and sometimes higher, as first time embryo transfers, pregnancy rates of 32 days in a group of recipients can result in 25-40% more pregnant recipient cows when compared to conventional pregnancy evaluation and resynchronization protocols.

The above disclosure is intended to be illustrative and not exhaustive. This description will suggest many variations and alternatives to one of ordinary skill in this art without departing from the scope of the present invention. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A method for breeding bovines, the method comprising the steps of:
    administering a first progesterone to a cow;
    removing the first progesterone from the cow;
    administering a means of conception to the cow after the first progesterone is removed, the means of conception selected from the group consisting of insemination and embryo implantation;
    administering a second progesterone to the cow after administering the means of conception to the cow; and
    performing an analysis on the cow to determine whether or not the cow is pregnant.

2. The method of claim 1, wherein the first progesterone is administered to the cow nine days before insemination.

3. The method of claim 2 further comprising the step of removing the first progesterone insert two days before insemination.

4. The method of claim 1, wherein the first progesterone is administered to the cow sixteen days before embryo implantation.

5. The method of claim 4 further comprising the step of removing the first progesterone insert seven days after the first progesterone is administered to the cow.

6. The method of claim 1, further comprising the step of administering a first gonadotropin releasing hormone to the cow the same day as the first progesterone insert is administered.

7. The method of claim 1, further comprising the step of administering a second gonadotropin releasing hormone to the cow nine days after the first gonadotropin releasing hormone is administered.

8. The method of claim 1, further comprising the step of administering prostaglandin F2α or cloprostenol to the cow before the means of conception is administered.

9. The method of claim 1, wherein the second progesterone is administered to the cow nineteen days after insemination.

10. The method of claim 1, wherein the second progesterone is administered to the cow twelve days after embryo implantation.

11. The method of claim 1, wherein the step of performing an analysis comprises performing ultrasound on the cow.

12. The method of claim 8, wherein the ultrasound is performed twenty six days after insemination.

13. The method of claim 8, wherein the ultrasound is performed nineteen days after embryo implantation.

14. The method of claim 1, wherein the step of performing an analysis comprises the steps of obtaining a biological sample from the cow and performing at least one assay on the biological sample.

15. The method of claim 10, wherein the biological sample is obtained between seven and thirty days after insemination.

16. A method for breeding bovines, the method comprising the steps of:
    administering a first progesterone to a cow;
    removing the first progesterone from the cow;
    implanting any embryo into the cow after the first progesterone is removed; and
    administering a second progesterone to the cow the same day as the embryo implantation.

17. The method of claim 16, wherein the first progesterone is administered to the cow sixteen days before embryo implantation.

18. The method of claim 16, further comprising the step of administering a first gonadotropin releasing hormone to the cow the same day as the first progesterone insert is administered.

19. The method of claim 8, further comprising the steps of removing the second progesterone from the cow, and performing an ultrasound on the cow between twenty-three and twenty-eight days after embryo implantation to determine whether or not the cow is pregnant.

20. The method of claim 19, wherein if the cow is determined not to be pregnant the method further comprising the step of implanting a second embryo into the cow.

* * * * *